United States Patent
Schütz

(10) Patent No.: US 8,416,916 B2
(45) Date of Patent: *Apr. 9, 2013

(54) METHOD AND APPARATUS FOR REPRESENTING AN X-RAY IMAGE

(75) Inventor: Oliver Schütz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1444 days.

This patent is subject to a terminal disclaimer.

(21) Appl. No.: 11/339,646

(22) Filed: Jan. 24, 2006

(65) Prior Publication Data

US 2006/0239411 A1    Oct. 26, 2006

(30) Foreign Application Priority Data

Jan. 24, 2005   (DE) .......................... 10 2005 003 226

(51) Int. Cl.
G01N 23/04    (2006.01)

(52) U.S. Cl. ................ 378/62; 378/98; 378/87; 600/410

(58) Field of Classification Search ................. 600/407, 600/410; 378/44, 51, 70, 86, 167; D24/158; 424/9.4
See application file for complete search history.

(56) References Cited

U.S. PATENT DOCUMENTS

| | | | | |
|---|---|---|---|---|
| 4,538,299 | A * | 8/1985 | DeForest | 382/197 |
| 4,730,212 | A * | 3/1988 | Wojcik et al. | 348/61 |
| 4,922,915 | A * | 5/1990 | Arnold et al. | 382/128 |
| 5,164,993 | A | 11/1992 | Capozzi et al. | |
| 5,544,219 | A * | 8/1996 | Muller et al. | 378/210 |
| 5,617,462 | A | 4/1997 | Spratt | |
| 6,018,565 | A * | 1/2000 | Ergun et al. | 378/95 |
| 6,067,343 | A | 5/2000 | Brendler et al. | |
| 6,404,846 | B1 | 6/2002 | Hasegawa et al. | |
| 6,497,511 | B1 * | 12/2002 | Schmitt et al. | 378/207 |
| 6,795,526 | B2 | 9/2004 | Kump et al. | |
| 7,274,770 | B2 * | 9/2007 | Nederpelt | 378/97 |
| 7,499,575 | B2 | 3/2009 | Böhm et al. | |
| 2003/0031300 | A1 * | 2/2003 | Cheng | 378/177 |
| 2003/0120145 | A1 * | 6/2003 | Schmitz et al. | 600/407 |
| 2004/0125921 | A1 | 7/2004 | Allouche et al. | |
| 2004/0125999 | A1 | 7/2004 | Iordache et al. | |
| 2005/0207535 | A1 | 9/2005 | Alving et al. | |
| 2007/0071173 | A1 | 3/2007 | Nederpelt | |

* cited by examiner

*Primary Examiner* — Tse Chen
*Assistant Examiner* — Joel F Brutus
(74) *Attorney, Agent, or Firm* — Schiff Hardin LLP

(57) ABSTRACT

In a method and an apparatus for representing an x-ray image of an examination subject, a measurement field is determined in the image field of the x-ray image, the measurement field being dependent on the position of a subject image region representing the examination subject in the image field and being essentially situated within this subject image region grey scale values for the image rendering are determined exclusively from the intensities measured within this measurement field.

8 Claims, 4 Drawing Sheets

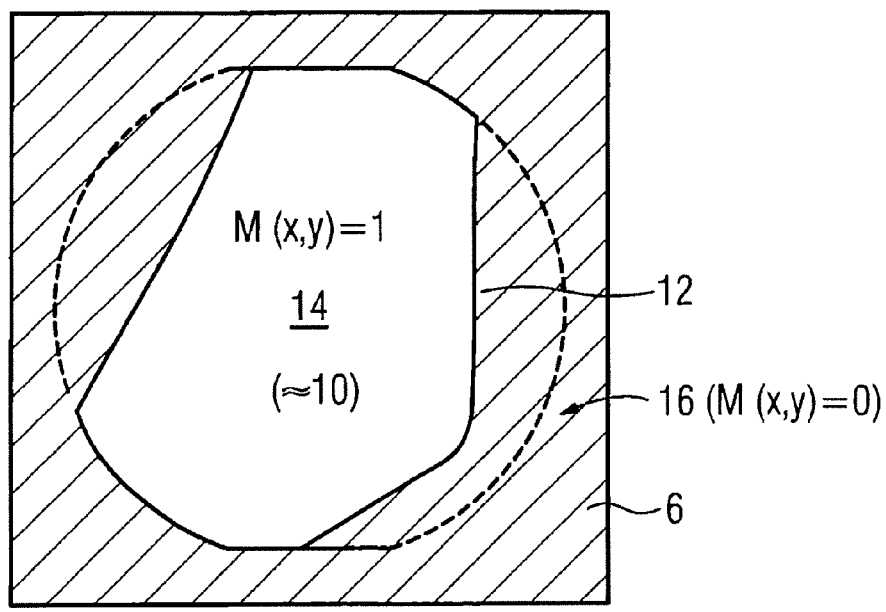
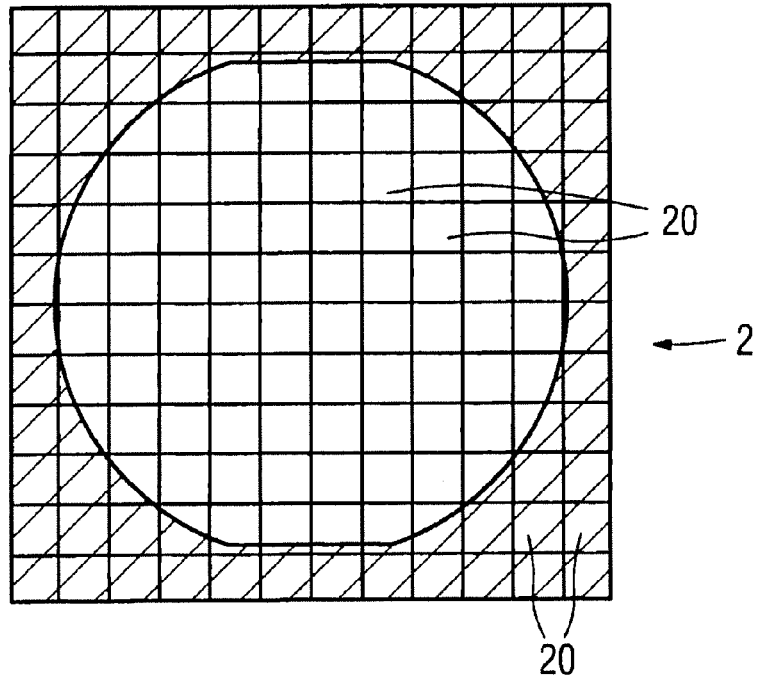

METHOD AND APPARATUS FOR REPRESENTING AN X-RAY IMAGE

BACKGROUND OF THE INVENTION

1. Field of the Invention

The present invention concerns a method and an apparatus for representing an x-ray image of an examination subject.

2. Description of the Prior Art

In the display rendering of x-ray images as they are acquired, for example, with a mobile C-arm x-ray apparatus, it is intended that image regions that are diagnostically relevant for the physician be shown with optimal quality on a monitor or in a presentation as a hard copy (film). This diagnostically relevant image region is formed by the region of the image field in which the image of the subject (the patient) is located. This region of the image field (designated in the following as the subject image region) is surrounded by regions that normally contain no diagnostic information. These are diaphragm-blanked regions as well as direct radiation regions in which x-rays are detected that have not penetrated the examination subject and thus are unattenuated.

Optimal quality means that the grey scale values within the subject image region enable an optimally differentiated, high-contrast representation of structures within this subject image region, with the representation being easily recognized and able for diagnostically evaluation. In contrast, the remaining image regions should be represented such that they do not hinder an observer. A primary problem in the representation of x-ray images is the direct radiation regions that occur with significant brightness in the x-ray image.

The image data at the output of an x-ray receiver (detector) that have already undergone pre-processing, so that the measured intensity I of the x-ray radiation is provided as a function of the image coordinates (x, y), normally exist with a resolution (for example 4096 intensity levels) that cannot be used by the representation medium (for example a monitor with 256 grey levels).

In order to achieve an image representation that is as optimal as possible, these intensity values must be mapped to the grey scale values that can be shown in the representation medium with apparatus-specific (normally non-linear) transformation rules (lookup characteristic curves or lookup tables). In other words, the grey scale values used for the image representation are associated with the respective intensities of the individual image points. For the determination of these grey scale values, the overall x-ray image is always evaluated in known x-ray apparatuses, because the presence or the position of direct radiation regions in the x-ray image is not known in advance. This has the consequence that the grey scale values in the subject image region are no longer shown with the best possible contrast resolution of the monitor, i.e. no longer utilizing the maximum possible grey scale values or grey level (gradation) range with, for example, 256 grey values, but instead are shown with fewer grey levels since, in the transformation, the extreme values (diaphragm region and direct radiation region) of the intensities measured by the x-ray receiver significantly limit the remaining grey scale value range available for the subject image region in the transformation.

Moreover, direct radiation regions that are present in the x-ray image can significantly mislead or distract or deceive the observer. The contrast resolution capability of the eye and the fine contrast detail in the subject image region are reduced when such direct radiation regions are reproduced on the monitor but are not recognized as such. Moreover, a darkening is always objectionable and should already be largely avoided for this reason.

The possibility exists in principle to minimize the direct radiation regions by the use of diaphragms (X-iris diaphragms or filter diaphragms). In practice, however, this possibility is not utilized because a correct adjustment of the diaphragm (in particular in the acquisition of a number of x-ray exposures from different directions) is time-consuming and moreover, adjustment of a diaphragm in a manner that prevents direct radiation regions without loss of diagnostic information is not possible in all cases due to a complex geometric shapes of the examination subject.

SUMMARY OF THE INVENTION

An object of the invention is a method and an apparatus for representing an x-ray image of an examination subject that generally avoid the aforementioned problems.

This object is achieved according to the invention by a method for representing an x-ray image of an examination subject, wherein a measurement field in the image field of the x-ray image is determined that is dependent on the position of a subject image region representing the examination subject in the x-ray image and that essentially lies within this subject image region, and grey scale values for the image overall representation are determined exclusively from the intensities measured within this measurement field. This ensures that the selection of the best possible lookup characteristic curve for the calculation of the grey values ensues only on the basis of the intensities measured essentially within the subject image region. Possibly present direct radiation regions can then no longer negatively influence the selection of the lookup characteristic curve.

As used herein, "curve" is used in the sense of representing a mathematical relation between two parameters, and thus encompasses a straight line representing a linear relationship.

As use herein, "intensity" means the intensity or attenuation or brightness value of an image point of image data for an image representation that are present at the output of an x-ray receiver. These images or, respectively, the associated image data have normally already been subjected to a pre-processing.

An additional assistance to the observer producing an improved perception capability of the details shown in the diagnostically-relevant image region is achieved in an embodiment wherein a direct radiation region situated outside of the subject image region is shown with a uniform appearance in the image representation. In other words, the direct radiation region can be unambiguously detected by a uniform appearance in the overall image, for example uniform color, uniform pattern or uniform darkening, and the attention and the eyes of the observer are not distracted or mislead or deceived, diagnostically-irrelevant image components are clearly identified. Such "virtual" diaphragms can be stored as an overlay together with the unprocessed image data. In principle, however, the image data can be stored already processed with a virtual diaphragm.

A particularly advantageous utilization of the available grey value range is achieved in an embodiment wherein the measurement field is entirely situated within the subject image region, i.e. when every point of the measurement field is also an image point of the examination subject.

In a preferred embodiment of the method, the measurement field is determined by a comparison of the intensity distribution of a calibration image generated in the absence of the examination subject with predetermined acquisition parameters (in particular with a predetermined x-ray dose) with the intensity distribution of a first x-ray image generated in the presence of the examination subject with these acquisition parameters. This enables a reliable division of the subject image region representing the examination subject in the x-ray image from the direct radiation region.

A particularly definite identification of the direct radiation or subject image region is achieved in an embodiment wherein the intensity distribution of a direct radiation image is measured in the absence of the examination subject and the intensity distribution of the calibration image is determined there from by multiplication of the intensity distribution of the direct radiation image with a scaling factor that is smaller than one.

In an embodiment of the method, the first x-ray image is compared point-by-point with the calibration image and the measurement field is formed by those image points having an intensity or brightness in the first x-ray image that is smaller than in the calibration image. This results in a measurement field being generated with a position and shape that substantially coincide with the position and shape of the subject image region representing the examination subject in the x-ray image.

As an alternative, a number of respective partial fields containing a plurality of image points is established in the image field. The measurement field is then formed by those partial fields in which the intensity of each image point in the first x-ray image is smaller than a threshold of the intensity that is respectively associated with these partial fields in the calibration image. Computing capacity and storage space are reduced by this embodiment.

Instead of such a point-by-point comparison implemented within the partial fields, the measurement field can be formed from those partial fields having a mean (average) intensity that is smaller in the first x-ray image than a threshold of the intensity that is respectively associated with these partial fields in the calibration image.

In practice, in particular with regard to the required computing capacity, it can also be appropriate to use partial fields that cover only a part of the image field.

The above object also is achieved by an apparatus according the invention that implements the embodiments of the method summarized above.

DESCRIPTION OF THE DRAWINGS

FIG. 3 shows a measurement field determined according to the invention.

FIG. 4 shows a direct radiation image generated in the absence of an examination subject and sub-divided into partial fields.

DESCRIPTION OF THE PREFERRED EMBODIMENTS

The x-ray images shown in the figures are images as they exist before a transformation to the displayable grey scale value range using a lookup characteristic curve, thus still with a high resolution with regard to their intensity, and merely serve for illustration of the inventive method and apparatus.

Figure 1:
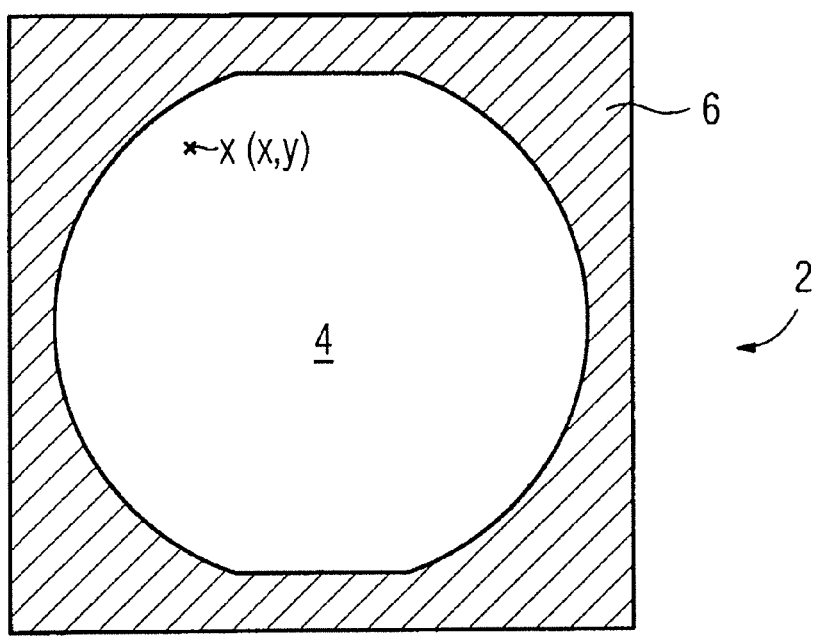
FIG. 1 shows a direct radiation image generated in the absence of an examination subject.

According to FIG. 1, an empty blank or direct radiation image 2 is generated in a first step with a predetermined set of acquisition parameters and in the absence of an examination subject. This direct radiation image 2 is composed of an approximately circular, brightly illuminated exposed image field 4 that is surrounded by a boundary region 6 generated with a diaphragm (for example a static aperture plate), an X-iris diaphragm or a filter diaphragm or with a mask used in digital image processing. This boundary region 6 is indicated in FIG. 1 with hatching and is not indicated in the following steps for determination of the measurement field. Moreover, for clarity the direct radiation image 2 is shown homogeneously white in FIG. 1. In practice, however, the intensity of the direct radiation in the image field 4 is not constant and moreover varies from apparatus to apparatus. The cause for this can be, for example, vignetting by the image intensifier, inhomogeneity of the beam filter, inhomogeneity of the x-ray radiation emitted by the x-ray source (Heel effect), or external interference sources.

The direct radiation image 2 can be processed by suitable digital image processing methods to reduce the image noise and to improve the image quality.

Since, in practice, given predetermined acquisition parameters the actual x-ray dose also can vary by several percent from exposure to exposure and the intensity distribution in the direct radiation image 2 can be influenced by further effects, the generated direct radiation images 2 are subjected to an additional post-processing in which the brightnesses or intensities of all image points are multiplied with a scaling factor (for example between 0.6 and 0.9). Such an effect is caused, for example, by variation of the spatial orientation of an image intensifier detector used as an x-ray receiver in an x-ray C-arm system (change of the position of the C-arm). Such a variation of the orientation of the image intensifier detector leads to an easy image rotation and image displacement, since the image intensifier detector is influenced by the Earth's magnetic field. The scaling factor is empirically determined for each system type or, each model or series. A calibration image is then obtained as a result from each direct radiation image 2.

Such a calibration image is advantageously generated and stored for all acquisition parameter sets, for example for every possible dose adjustment. In some circumstances, however, it may not be necessary to generate and store a calibration image for every possible dose setting, but rather merely to generate and store only a calibration image at well-defined, larger dose intervals. The generation of the calibration images is preferably implemented at the manufacturer before the delivery of the x-ray system, and the calibration images as well as the associated acquisition data are permanently stored in the x-ray system. Due to unavoidable aging effects, however, it can be appropriate to update the calibration from time to time, for example after one or two years.

Figure 2:
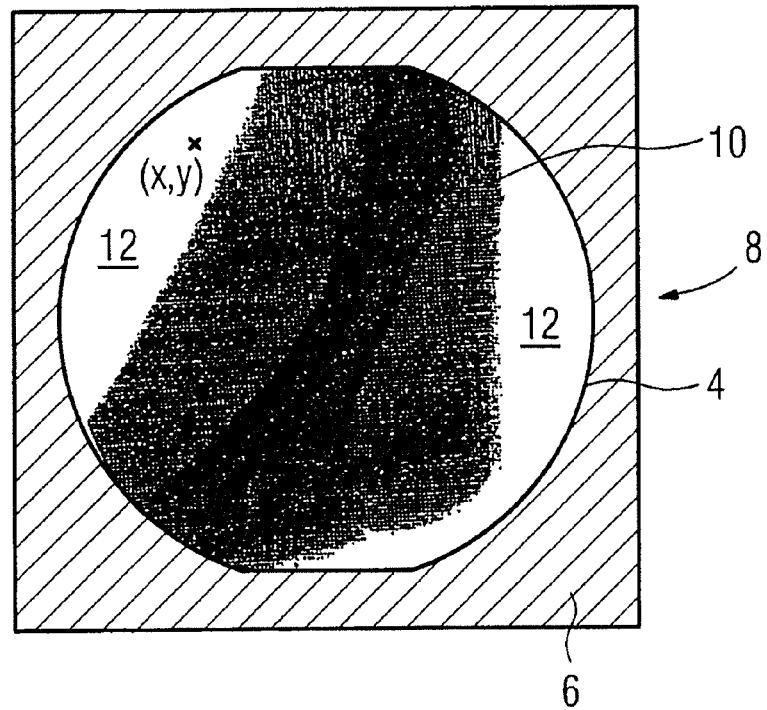
FIG. 2 shows a first x-ray image generated in the presence of an examination subject.

As shown in FIG. 2, a first x-ray image 8 is now generated in the presence of an examination subject in a second step. In the FIG. 2 it can be seen that this examination subject only occupies a subject image region 10 of a usable image field 4 situated within the screened boundary region 6, which subject image region 10 is smaller than the image field 4. Due to the smaller measurements of the examination subject, direct radiation regions 12 that brighten the image field 4 are located in the image field 4 in addition to this object image region 10. Given the use of a look-up table for the transformation (required for image rendering) of the measured intensities into grayscale values, these direct radiation regions 12 would limit the grayscale level available for the object image region 10 and lead to a non-optimal rendering.

The image field 4 of the first x-ray image 8 is now compared image point-by-image point with the calibration image 5 belonging to this acquisition parameter set. Each image point (x, y) of the first x-ray image 8 whose intensity $I_R(X, y)$ is smaller than the intensity $I_K(X, y)$ in the corresponding calibration image belongs to the subject image region 10. Each image point (x, y) in the first x-ray image 8 whose intensity $I_R(X, y)$ is greater than or equal to the intensity $I_K(X, y)$ in the corresponding calibration image is, with high probability, direct radiation and does not belong to the subject image region 10.

From such a point-by-point comparison of the intensities, a subject mask M(x, y) is formed that practically contains only the subject image region 10. This subject mask M(x, y) is formed according to the following rule:

If $(I_R(x, y) < I_K(x, y)$ then M(x, y)=1
otherwise M(x, y)=0.

All image points of the subject mask M that belong to the subject image region 10 and thus to the examination subject are thus occupied with the value "1"; the other regions receive the value "0". The measurement field for the choice of the look-up transformation is now formed by those image points x, y for which: M(x, y)=1.

In order to enable a good separation between subject image region 10 and direct radiation region 12 with the method explained in the preceding, it is appropriate to use the first x-ray image in its raw form, thus before the execution of digital image processing or image improvement methods.

A measurement field 14 generated by point-by-point comparison is shown in FIG. 3 and approximately corresponds in terms of its shape and area to the shape and area of the subject image region 10. The remainder region 16 formed from direct radiation region 12 and boundary region 6 (indicated by hatching) is not used as a measurement field 14. This is formed by image points (x, y) for which: M(x, y)=0. The remainder region 16 can be used as a virtual diaphragm in the representation and be shown in a uniform manner, for example darkened with a homogenous grey scale value or with uniform color or with a uniform pattern.

For the measurement field 14 determined in this manner, based on the intensity distribution I(x, y) present in this measurement field 14, the lookup table to be used for the best possible visualization or image rendering or transformation rule T for transformation of the intensity values I in grey values G $$T:I(x,y) \rightarrow G(x,y)$$

is now selected according to known algorithms implemented in the image processing software of the x-ray apparatus, and the entire grey level range available for the selected rendering medium (normally a monitor) can be utilized. From time to time, for example given a spatial variation of the examination subject, it can be necessary to effect a new determination of the measurement field. In principle, however, it is appropriate to re-determine the measurement field given each x-ray acquisition and to use the re-determined measurement field for the optimized rendering of the next x-ray acquisition.

In the direct radiation image 2 shown in the exemplary embodiment according to FIG. 4, the entire image field 4 is separated into a plurality of quadratic partial fields 20. A threshold $I_S$ of the intensity is now determined for each of these partial fields 20. For example, an arithmetic mean or a median value of the intensities of all image points in the partial field 20 is formed and multiplied with a scaling factor to form this threshold $I_S$. As an alternative, the threshold $I_S$ is determined in that the minimal intensity value is determined and multiplied with a scaling factor within each partial field 20. In other words: a calibration image is generated in which only one threshold $I_S$ is associated with each partial field 20.

Figure 5:
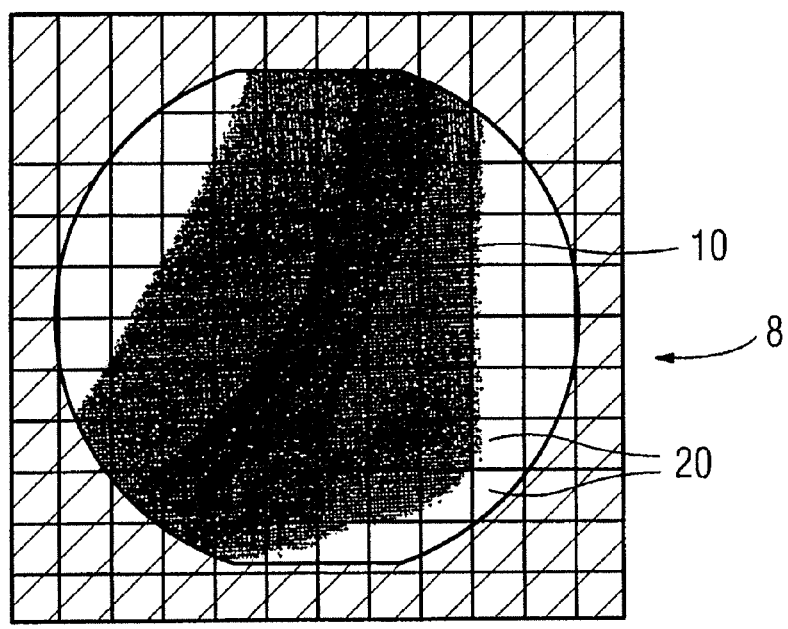
FIG. 5 shows a first x-ray image generated in the presence of the examination subject and likewise divided into partial fields.

According to FIG. 5, a first x-ray image is now likewise generated in the presence of the examination subject in a subsequent step and the acquired image is likewise sub-divided into the same partial fields 20.

Figure 6:
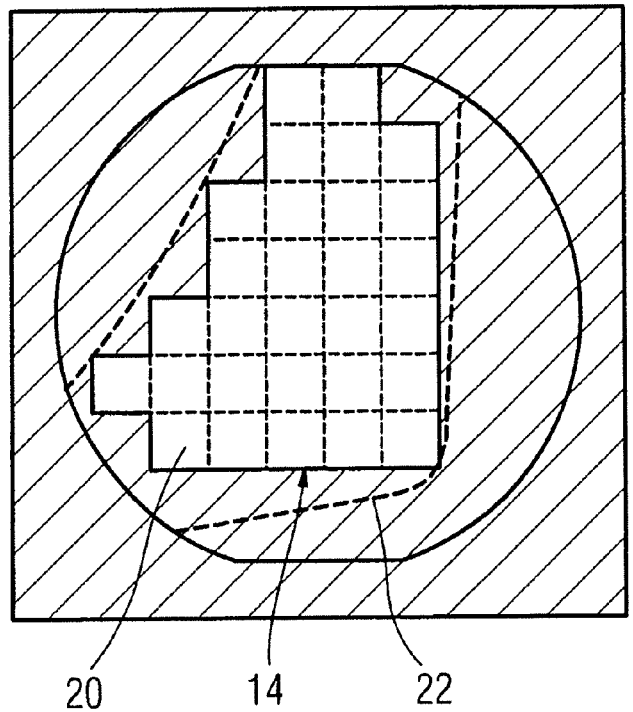
FIG. 6 shows a measurement field assembled according to the invention from a number of partial fields.

The formation of the measurement field 14 ensues analogously to the procedure illustrated in the preceding, whereby in the shown exemplary embodiment only those partial fields 20 in which each image point (x, y) within the partial field 20 exhibits an intensity $I_R(x, y)$ that is smaller than the threshold $I_S$ of the intensity of this partial field 20 in the calibration image are considered as belonging to the measurement field 14. Partial fields 20 that overlap with the subject image region 10 only in one partial region are thus not associated with the measurement field 14. The measurement field 14 shown in FIG. 6 is created in this manner. The measurement field 14 lies exclusively within the subject image region 10 reproducing the examination subject. The contour 22 of the subject image region 10 is indicated dashed in the FIG. 6. In other words: the measurement field 14 lies completely within the subject image region 10. The subject image region 10 and the measurement field 14 then do not entirely coincide, corresponding to the rough raster of the partial fields 20. In this exemplary embodiment, the remainder region 16 situated outside of the measurement field 14 can no longer be used as a virtual diaphragm, because then parts of the subject would be missing in the image reproduction. Only in the case of very small partial fields 20 can it be appropriate to use the remainder region 16 as a virtual diaphragm.

As an alternative to this procedure, a mean intensity can also be determined for each partial field 20 in the first x-ray image and compared with the respective thresholds $I_S$ belonging to these partial fields 20. Only those partial fields whose mean intensity is smaller than the mean intensity of the corresponding partial field of the calibration image are then used for the measurement field. In this manner a measurement field would be created that is negligibly larger than the subject image region and also would contain partial fields at the edge of the subject image region that do not entirely lie within the subject image region.

Figure 7:
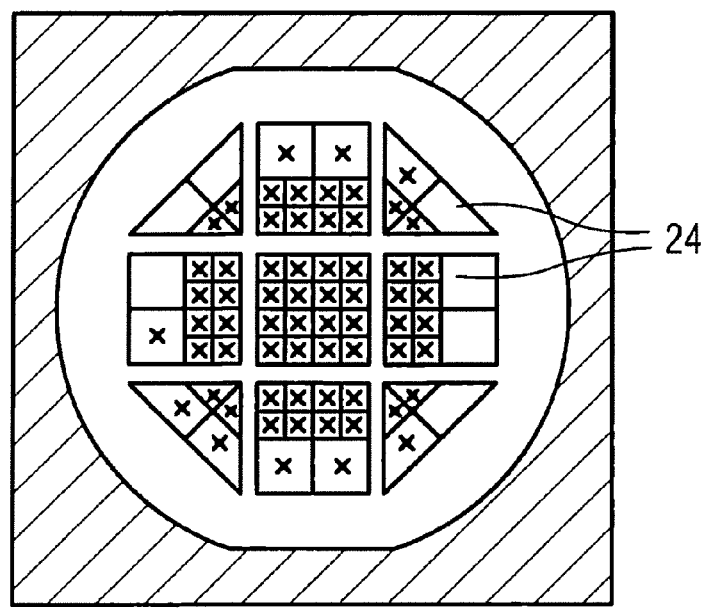
FIG. 7 shows an alternative distribution of the partial fields in the image field.

As an alternative to the methods respectively shown in FIGS. 1 through 3 and 4 through 6, in which the entire image field is selected for determination of the measurement field 14, in the exemplary embodiment explained in FIG. 7, partial fields 24 of different sizes and different shapes are used that cover only a part of the usable image field. In this exemplary embodiment, the selection of the partial fields 24 forming the measurement field also ensues with the algorithms described using FIG. 4 though 6. In this exemplary embodiment, the measurement field 14 is then formed by the partial fields 24 (provided with a cross) when, as in the first variants explained using FIGS. 4-6, only those partial fields 24 that contain no image point whose intensity in the calibration image is larger than the intensity of the associated image point of the first x-ray image are considered.

Figure 8:
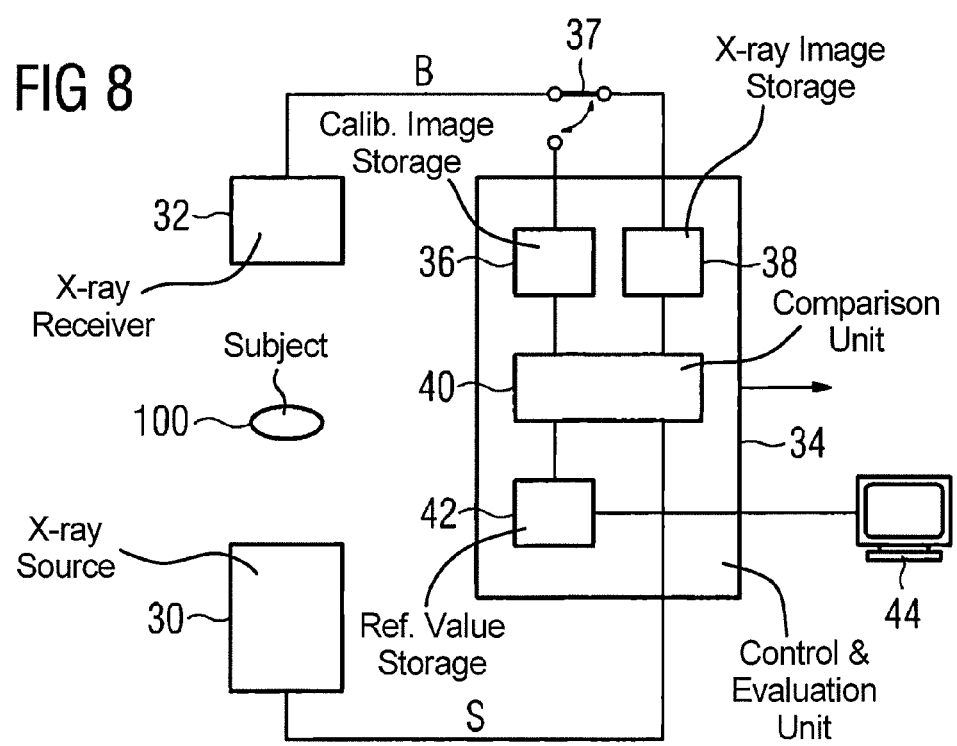
FIG. 8 is a block of diagram of apparatus according to the invention.

According to FIG. 8, an apparatus for generation of an x-ray image of an examination subject 100 comprises an x-ray source 30 and an x-ray receiver 32. The image data B acquired (and, if applicable, post-processed) by the x-ray receiver 32 are supplied to an evaluation device 34 for evaluation of the image data B. The evaluation device 34 comprises a calibration image storage 36 in which are stored a plurality of respective calibration images associated with an acquisition parameter set. These calibration images are generated from direct radiation images in a calibration mode according to the methods explained above, these direct radiation images having been determined for different acquisition parameter sets in the absence of the examination subject 100. The x-ray image of the examination subject 100 that was measured in a normal mode with a preset acquisition parameter set (symbolically represented by the closed selector switch) and stored in an x-ray image storage 38 is compared in a comparison device 40 with the stored calibration image belonging to this acquisition parameter set, and a measurement field is selected according to the algorithms explained in the preceding. The grey scale values necessary for image rendering in an image rendering medium 44 (a monitor in the exemplary embodiment) are then determined for this measurement field in an image processing device 42.

Moreover, an evaluation of the image data B for generation of a control signal S for the dose control of the x-ray source 30 ensues in the evaluation device 34.

I claim as my invention:

1. A method for rendering an image comprising the steps of:
   Emitting x-rays from an x-ray source, using predetermined imaging parameters, to obtain a direct radiation image without any imageable object in a path of said x-rays, and generating a calibration image from said direction radiation range, said calibration image having an intensity distribution;
   generating an x-ray image of an examination subject using said predetermined image acquisition parameters, said x-ray image having an intensity distribution and having an image field containing a subject image region representing the examination subject;
   automatically determining said intensity distribution of said x-ray image of said examination subject;
   in a computerized processor, automatically determining a measurement field in said image field of said x-ray image, by comparing the intensity distribution of said calibration image with the intensity distribution of said x-ray image of the examination subject; and
   in said processor, automatically determining grey scale values for visually representing said x-ray image exclusively from intensities in said measurement field.

2. A method as claimed in claim 1 wherein said x-ray image contains a direct radiation region, and comprising representing said direct radiation region with a uniform appearance when visually representing said x-ray image.

3. A method as claimed in claim 1, comprising determining said measurement field as being completely situated within said subject image region in said image field.

4. A method as claimed in claim 1, wherein the step of generating said calibration image comprises obtaining a direct radiation without said examination subject image and automatically electronically determining said intensity distribution of said calibration image by multiplying an intensity distribution of said direct radiation image with scaling factor that is less than 1.

5. A method as claimed in claim 1, comprising comparing said calibration image and said x-ray image of said examination subject pixel-by-pixel, and automatically electronically forming said measurement field from pixels in said x-ray image of the examination subject, having a characteristic selected from the group consisting of intensity and a brightness, that is less than said characteristic of a corresponding pixel in said calibration image.

6. A method as claimed in claim 1, comprising automatically electronically defining a plurality of partial fields, each containing a plurality of pixels, in each of said image fields and said x-ray image of said examination subject and said calibration image, and automatically electronically forming said measurement field from partial fields, among said plurality of partial fields in said x-ray image of the examination subject, wherein an intensity of each pixel is less than a threshold intensity of a corresponding partial field in said calibration image.

7. A method as claimed in claim 1, comprising automatically electronically defining a plurality of partial fields, each containing a plurality of pixels, in each of said image fields and said x-ray image of said examination subject and said calibration image, and automatically electronically forming said measurement field from partial fields, among said plurality of partial fields in said x-ray image of the examination subject, having an average intensity that is less than a threshold intensity of a corresponding partial field in said calibration image.

8. An apparatus for generating a diagnostic x-ray image of an examination subject, comprising:
   an x-ray source adapted to emit x-rays that penetrate an examination subject;
   an x-ray receiver on which x-rays from said x-ray source are incident, said x-rays incident on said x-ray receiver comprising x-rays that have penetrated the examination subject and x-rays that have not penetrated the examination subject, said x-ray receiver emitting electrical signals corresponding to the x-rays incident thereon;
   a control and evaluation unit supplied with said electrical signals from said x-ray receiver, said control and evaluation unit forming an x-ray image, having an intensity distribution, of the examination subject from the electronic signals, said x-ray image having an image field containing a subject image region representing the examination subject, said control and evaluation unit determining a measurement field dependent on a position of said subject image region in said image field and that is substantially situated within said subject image region, and determining grey scale values for visually representing said x-ray image exclusively from said measurement field;
   said control and evaluation unit being configured to operate said x-ray source to generate a direct radiation image without any imageable object in a path of said x-rays and to obtain a calibration image from said direct radiation image, said calibration image having an intensity distribution;
   a memory accessible by said control and evaluation unit in which said calibration image is stored; and
   said control and evaluation unit being configured to access said calibration image stored in said memory and to compare said intensity distribution of said x-ray image of the examination subject with said intensity distribution of said calibration image to obtain a comparison result, and to use said comparison result to determine said measurement field.

* * * * *